United States Patent
Ben Nun

(10) Patent No.: US 8,398,709 B2
(45) Date of Patent: Mar. 19, 2013

(54) ACCOMMODATING INTRAOCULAR LENS (AIOL) CAPSULES

(75) Inventor: Joshua Ben Nun, D.N. Vitkin (IL)

(73) Assignee: Nulens Ltd., Herzliya Pituah (IL)

(*) Notice: Subject to any disclaimer, the term of this patent is extended or adjusted under 35 U.S.C. 154(b) by 159 days.

(21) Appl. No.: 13/001,597

(22) PCT Filed: Jul. 26, 2009

(86) PCT No.: PCT/IL2009/000728
§ 371 (c)(1), (2), (4) Date: Dec. 27, 2010

(87) PCT Pub. No.: WO2010/010565
PCT Pub. Date: Jan. 28, 2010

(65) Prior Publication Data
US 2011/0112636 A1    May 12, 2011

(30) Foreign Application Priority Data

Jul. 24, 2008  (IL) .......................................... 193021
Mar. 22, 2009  (IL) .......................................... 197742

(51) Int. Cl.
*A61F 2/16* (2006.01)
(52) U.S. Cl. ...................................................... 623/6.37
(58) Field of Classification Search .................. 623/4.1, 623/6.11, 6.13, 6.22, 6.37
See application file for complete search history.

(56) References Cited

U.S. PATENT DOCUMENTS

| | | |
|---|---|---|
| 3,950,082 A | 4/1976 | Volk |
| 4,122,556 A | 10/1978 | Poler |
| 4,254,509 A | 3/1981 | Tennant |
| 4,298,994 A | 11/1981 | Clayman |
| 4,340,979 A | 7/1982 | Kelman |
| 4,409,690 A | 10/1983 | Gess |
| 4,409,691 A | 10/1983 | Levy |
| 4,445,998 A | 5/1984 | Kanda et al. |
| 4,446,581 A | 5/1984 | Blake |
| 4,494,254 A | 1/1985 | Lopez |
| 4,530,117 A | 7/1985 | Kelman |
| RE31,963 E | 8/1985 | Kelman |
| 4,556,998 A | 12/1985 | Siepser |

(Continued)

FOREIGN PATENT DOCUMENTS

| | | |
|---|---|---|
| EP | 0 156 472 A | 10/1985 |
| EP | 0637503 B1 | 10/1998 |

(Continued)

OTHER PUBLICATIONS

Chu, Ralph Y. and Buliano, Megan, Accommodating IOLS by Ralph Chu et al, Cataract & Refractive Surgery Today, May 2004.

(Continued)

*Primary Examiner* — William H. Matthews
*Assistant Examiner* — Howie Matthews
(74) *Attorney, Agent, or Firm* — Morgan, Lewis & Bockius LLP

(57) ABSTRACT

Accommodating intraocular lens (AIOL) capsules having a continuously variable Diopter strength between a first Diopter strength in a non-compressed state and a second Diopter strength different than its first Diopter strength in a compressed state. The AIOL capsules include an anterior capsule plate, a posterior capsule plate, and a capsule ring for bounding a hermetic cavity filled with a capsule filling. The anterior capsule plate is intended to anteriorly bulge along the human eye's visual axis on application of an axial compression force against the posterior capsule plate from a posterior direction.

10 Claims, 14 Drawing Sheets

U.S. PATENT DOCUMENTS

| | | | |
|---|---|---|---|
| 4,575,374 | A | 3/1986 | Anis |
| 4,581,033 | A | 4/1986 | Callahan |
| 4,589,147 | A | 5/1986 | Nevyas |
| 4,591,358 | A | 5/1986 | Kelman |
| 4,615,701 | A | 10/1986 | Woods |
| 4,671,283 | A | 6/1987 | Hoskin et al. |
| 4,676,794 | A | 6/1987 | Kelman |
| 4,750,904 | A | 6/1988 | Price, Jr. |
| 4,808,181 | A | 2/1989 | Kelman |
| 4,842,601 | A | 6/1989 | Smith |
| RE33,039 | E | 8/1989 | Arnott |
| 4,865,601 | A | 9/1989 | Caldwell et al. |
| 4,888,012 | A | 12/1989 | Horn et al. |
| 4,892,543 | A | 1/1990 | Turley |
| 4,932,966 | A | 6/1990 | Christie et al. |
| 4,932,968 | A | 6/1990 | Caldwell et al. |
| 4,957,505 | A | 9/1990 | McDonald |
| 4,969,897 | A | 11/1990 | Kalb |
| 4,976,732 | A | 12/1990 | Vorosmarthy |
| 4,990,159 | A | 2/1991 | Kraff |
| 5,026,373 | A | 6/1991 | Ray |
| 5,078,742 | A | 1/1992 | Dahan |
| 5,171,268 | A | 12/1992 | Ting et al. |
| 5,176,701 | A | 1/1993 | Dusek et al. |
| 5,275,623 | A | 1/1994 | Sarfarazi |
| 5,282,851 | A | 2/1994 | Jacob-LaBarre |
| 5,288,293 | A | 2/1994 | O'Donnell, Jr. |
| 5,336,262 | A | 8/1994 | Chu |
| 5,346,502 | A | 9/1994 | Estabrook et al. |
| 5,476,512 | A | 12/1995 | Sarfarazi |
| 5,476,514 | A | 12/1995 | Cumming |
| 5,476,515 | A | 12/1995 | Kelman et al. |
| 5,480,426 | A | 1/1996 | Chu |
| 5,484,447 | A | 1/1996 | Waldock et al. |
| 5,489,302 | A | 2/1996 | Skottun |
| 5,496,366 | A | 3/1996 | Cumming |
| 5,522,891 | A | 6/1996 | Klaas |
| 5,567,365 | A | 10/1996 | Weinschenk et al. |
| 5,571,177 | A | 11/1996 | Deacon et al. |
| 5,584,304 | A | 12/1996 | Brady |
| 5,607,472 | A | 3/1997 | Thompson |
| 5,628,795 | A | 5/1997 | Langerman |
| 5,674,282 | A | 10/1997 | Cumming |
| 5,684,637 | A | 11/1997 | Floyd |
| 5,722,952 | A | 3/1998 | Schachar |
| 5,752,960 | A | 5/1998 | Nallakrishnan |
| 5,766,244 | A | 6/1998 | Binder |
| 5,843,188 | A | 12/1998 | McDonald |
| 5,871,455 | A | 2/1999 | Ueno |
| 5,895,610 | A | 4/1999 | Chang |
| 5,919,230 | A | 7/1999 | Sambursky |
| 5,968,094 | A | 10/1999 | Werblin et al. |
| 5,984,962 | A | 11/1999 | Anello |
| 6,007,579 | A | 12/1999 | Lipshitz et al. |
| 6,027,531 | A | 2/2000 | Tassignon |
| 6,051,024 | A | 4/2000 | Cumming |
| 6,110,202 | A | 8/2000 | Barraquer et al. |
| 6,117,171 | A | 9/2000 | Skottun |
| 6,129,759 | A | 10/2000 | Chambers |
| 6,164,282 | A | 12/2000 | Gwon et al. |
| 6,193,750 | B1 | 2/2001 | Cumming |
| 6,197,057 | B1 | 3/2001 | Peyman et al. |
| 6,197,059 | B1 | 3/2001 | Cumming |
| 6,200,342 | B1 | 3/2001 | Tassignon |
| 6,280,469 | B1 | 8/2001 | Terry et al. |
| 6,280,471 | B1 | 8/2001 | Peyman et al. |
| 6,299,618 | B1 | 10/2001 | Sugiura |
| 6,299,641 | B1 | 10/2001 | Woods |
| 6,342,073 | B1 | 1/2002 | Cumming et al. |
| 6,387,126 | B1 | 5/2002 | Cumming |
| 6,406,494 | B1 | 6/2002 | Laguette et al. |
| 6,423,094 | B1 | 7/2002 | Sarfarazi |
| 6,443,984 | B1 | 9/2002 | Jahn et al. |
| 6,443,985 | B1 | 9/2002 | Woods |
| 6,464,725 | B2 | 10/2002 | Skottun |
| 6,488,708 | B2 | 12/2002 | Sarfarazi |
| 6,494,910 | B1 | 12/2002 | Ganem et al. |
| 6,494,911 | B2 | 12/2002 | Cumming |
| 6,503,276 | B2 | 1/2003 | Lang et al. |
| 6,506,212 | B2 | 1/2003 | Zhou et al. |
| 6,520,691 | B2 | 2/2003 | Nomura et al. |
| 6,524,340 | B2 | 2/2003 | Israel |
| 6,554,860 | B2 | 4/2003 | Hoffmann et al. |
| 6,570,718 | B2 | 5/2003 | Nomura et al. |
| 6,596,026 | B1 | 7/2003 | Gross et al. |
| 6,599,317 | B1 | 7/2003 | Weinschenk, III et al. |
| 6,605,093 | B1 | 8/2003 | Blake |
| 6,616,692 | B1 | 9/2003 | Glick et al. |
| 6,638,305 | B2 | 10/2003 | Laguette |
| 6,638,306 | B2 | 10/2003 | Cumming |
| 6,645,245 | B1 | 11/2003 | Preussner |
| 6,739,722 | B2 | 5/2004 | Laguette et al. |
| 6,749,634 | B2 | 6/2004 | Hanna |
| 6,790,232 | B1 | 9/2004 | Lang |
| 6,849,091 | B1 | 2/2005 | Cumming |
| 6,960,231 | B2 | 11/2005 | Tran |
| 6,972,033 | B2 | 12/2005 | McNicholas |
| 7,008,449 | B2 | 3/2006 | Willis et al. |
| 7,025,783 | B2 | 4/2006 | Brady et al. |
| 7,037,338 | B2 | 5/2006 | Nagamoto |
| 7,097,660 | B2 | 8/2006 | Portney |
| 7,118,597 | B2 | 10/2006 | Miller et al. |
| 7,122,053 | B2 | 10/2006 | Esch |
| 7,137,994 | B2 | 11/2006 | De Juan, Jr. |
| 7,220,279 | B2 | 5/2007 | Nun |
| 7,261,737 | B2 | 8/2007 | Esch et al. |
| 7,278,739 | B2 | 10/2007 | Shadduck |
| 7,350,916 | B2 | 4/2008 | Hong et al. |
| 7,815,678 | B2 | 10/2010 | Ben Nun |
| 7,842,087 | B2 | 11/2010 | Ben Nun |
| 7,854,764 | B2 | 12/2010 | Ben Nun |
| 7,976,520 | B2 | 7/2011 | Ben Nun |
| 7,998,199 | B2 | 8/2011 | Ben Nun |
| 8,048,156 | B2 | 11/2011 | Geraghty et al. |
| 2002/0103535 | A1 | 8/2002 | Portney |
| 2002/0103537 | A1 | 8/2002 | Willis et al. |
| 2003/0060881 | A1 | 3/2003 | Glick et al. |
| 2003/0097177 | A1 | 5/2003 | Tran |
| 2003/0109926 | A1 | 6/2003 | Portney |
| 2003/0149480 | A1 | 8/2003 | Shadduck |
| 2004/0073304 | A1 | 4/2004 | Weinschenk, III et al. |
| 2004/0148022 | A1 | 7/2004 | Eggleston |
| 2004/0169816 | A1 | 9/2004 | Esch |
| 2004/0181279 | A1 | 9/2004 | Nun |
| 2005/0090896 | A1 | 4/2005 | Ben Nun |
| 2005/0177229 | A1 | 8/2005 | Boxer Wachler |
| 2006/0069431 | A1 | 3/2006 | Graney et al. |
| 2006/0069433 | A1 | 3/2006 | Nun |
| 2006/0074487 | A1 | 4/2006 | Gilg |
| 2007/0027538 | A1 | 2/2007 | Aharoni et al. |
| 2007/0027541 | A1 | 2/2007 | Aharoni et al. |
| 2007/0088433 | A1 | 4/2007 | Esch et al. |
| 2007/0093891 | A1 | 4/2007 | Tabernero |
| 2007/0123981 | A1 | 5/2007 | Tassignon |
| 2007/0129799 | A1 | 6/2007 | Schedler |
| 2007/0129801 | A1 | 6/2007 | Cumming |
| 2007/0129803 | A1 | 6/2007 | Cumming |
| 2007/0185574 | A1 | 8/2007 | Ben Nun |
| 2007/0244561 | A1 | 10/2007 | Ben Nun |
| 2008/0004699 | A1 | 1/2008 | Ben Nun |
| 2008/0188930 | A1 | 8/2008 | Mentak et al. |
| 2008/0300680 | A1 | 12/2008 | Ben Nun |
| 2009/0198247 | A1 | 8/2009 | Ben Nun |
| 2009/0264998 | A1 | 10/2009 | Mentak et al. |
| 2010/0121444 | A1 | 5/2010 | Ben Nun |

FOREIGN PATENT DOCUMENTS

| | | |
|---|---|---|
| EP | 1 321 112 A | 6/2003 |
| FR | 2 794 965 | 12/2000 |
| JP | 2005007029 | 1/2005 |
| TW | 523408 | 3/2003 |
| WO | WO 83/00998 | 3/1983 |
| WO | WO 94/28825 | 12/1994 |
| WO | WO 95/20367 | 8/1995 |
| WO | WO 98/05273 | 2/1998 |
| WO | WO 98/10717 | 3/1998 |
| WO | WO 99/62434 | 12/1999 |

| | | |
|---|---|---|
| WO | WO 00/30566 | 6/2000 |
| WO | WO 00/61036 | 10/2000 |
| WO | WO 00/66037 | 11/2000 |
| WO | WO 01/08606 | 2/2001 |
| WO | WO 01/60286 | 8/2001 |
| WO | WO 02/065951 | 8/2002 |
| WO | WO 03/000154 | 1/2003 |
| WO | WO 03/015669 | 2/2003 |
| WO | WO 2005/104994 | 11/2005 |
| WO | WO 2006/040759 | 4/2006 |
| WO | WO 2006/103674 | 10/2006 |
| WO | WO 2007/048615 | 5/2007 |
| WO | WO 2008/023379 | 2/2008 |
| WO | WO 2008/083283 A2 | 7/2008 |
| WO | WO 2008/097915 | 8/2008 |
| WO | WO 2008/107882 | 9/2008 |
| WO | WO 2009/122409 | 10/2009 |
| WO | WO 2010/010565 | 1/2010 |
| WO | WO 2012/023133 | 2/2012 |

OTHER PUBLICATIONS

Notification of Transmittal of the International Preliminary Report on Patentability for PCT/IL2009/000728 filed Jul. 26, 2009 (having a priority date of Jul. 24, 2008).

US 8,398,709 B2

ACCOMMODATING INTRAOCULAR LENS (AIOL) CAPSULES

RELATED APPLICATIONS

The present application is a U.S. National Phase Application of International Application PCT/IL2009/000728, filed on 26 Jul. 2009 which is herein incorporated by reference in its entirety.

FIELD OF THE INVENTION

The invention pertains to accommodating intraocular lenses (AIOLs).

BACKGROUND OF THE INVENTION

Commonly owned PCT International Application No. PCT/IL02/00693 entitled Accommodating Lens Assembly and published on 27 Feb. 2003 under PCT International Publication No. WO 03/015669 illustrates and describes accommodating intraocular lens (AIOL) assemblies, the contents of which are incorporated herein by reference. The AIOL assemblies each include a haptics system adapted to be securely fixed in a human eye's annular ciliary sulcus at at least two spaced apart stationary anchor points so that it may act as a reference plane for an AIOL of continuously variable Diopter strength affected by a human eye's capsular diaphragm under control of its sphincter-like ciliary body and acting thereagainst from a posterior direction. The haptics systems include a rigid planar haptics plate with a telescoping haptics member for sliding extension. The AIOL may not necessarily be made of a single component or material. For example, the AIOL may be in the form of a sac filled with a fluid or gel. The haptics plate and the haptics member are preferably self-anchoring as illustrated and described in commonly owned PCT International Application No. PCT/IL02/00128 entitled Intraocular Lens and published on 29 Aug. 2002 under PCT International Publication No. WO 02/065951, the contents of which are incorporated herein by reference.

Commonly owned CT International Application No. PCT/IL2005/000456 entitled Accommodating Intraocular Lens Assemblies and Accommodation Measurement Implant and published on 10 Nov. 2005 under PCT International Publication No. WO 2005/104994 illustrates and describes AIOL assemblies enabling post implantation in situ manual selective displacement of an AIOL along a human eye's visual axis relative to at least two spaced apart stationary anchor points to a desired position to ensure that an AIOL assumes a non-compressed state in a human eye's constricted ciliary body state, the contents of which are incorporated herein by reference. Such in situ manual selective displacement can be effected post implantation to correct for capsular contraction which is a natural reaction which typically develops over a few months following extraction of the contents of a human eye's natural crystalline lens, and also a subject's changing eyesight overtime with minimal clinical intervention. Such in situ manual selective displacement can be achieved as follows: First, a discrete haptics system for retaining a discrete AIOL which is manually displaceable relative thereto. And second, a haptics system with at least two haptics having radiation sensitive regions capable of undergoing plastic deformation for in situ manual displacement of an integrally formed AIOL.

Commonly owned PCT International Application No. PCT/IL2006/000406 entitled Accommodating Intraocular Lens (AIOL) Assemblies, and Discrete Components Therefor published on 5 Oct. 2006 under PCT International Publication No. WO 2006/103674 illustrates and describes AIOL assemblies enabling post implantation in situ manual selective displacement of an AIOL along a human eye's visual axis relative to at least two spaced apart stationary anchor points to a desired position to ensure that an AIOL assumes a non-compressed state in a human eye's constricted ciliary body state, the contents of which are incorporated herein by reference. WO 2006/103674 still further illustrates and describes preferred attachment plates for self-anchoring implantation in a human eye's annular ciliary sulcus (see FIG. 4).

WO 2006/103674 further illustrates and describes an AIOL including a 25 housing formed from a rigid bio-compatible material and having side apertures. The housing contains a pair of shape memory disc-like optical elements including a leading optical element and a trailing optical element. The trailing optical element is intended to bulge into, the leading optical element which is intended to radially bulge through the housing's side apertures.

Commonly owned PCT International Application No. PCT/IL2008/000284 entitled Unitary Accommodating Intraocular Lenses (AIOLs) and Discrete Members For Use Therewith published on 12 Sep. 2008 under PCT International Publication No. 2008/107882 illustrates and 5 describes unitary AIOLs intended to be used in conjunction with either a purpose designed discrete base member implanted immediately prior to an AIOL typically during the same surgical procedure or a previously implanted standard in-the-bag IOL acting as a discrete base member, the contents of which are incorporated by reference. Alternatively, the unitary AIOLs can be designed to be solely used 10 with purpose designed discrete base members. The unitary AIOLs preferably include a so-called Vertical Adjustment Mechanism (VAM) for enabling in situ longitudinal displacement of their optical elements relative to their stationary anchoring points. The VAMs are implemented by each haptics including a radiation sensitive rod for introducing localized heating.

Purpose designed discrete base members have an elongated substantially planar main body with opposite leading and trailing ends. The base members have a central piston member and lateral wings with a tapering thickness such that they are readily flexible to conform to the natural curvature of a human eye's capsular diaphragm on implantation. The piston members are preferably formed 20 with an alignment element for axially aligning a unitary AIOL with a discrete base member on implantation in a human eye. Additionally, the piston members can be formed with a rounded bulge control core for both alignment purposes and also assisting in the controlled anterior bulging of an AIOL having an optical element with a posterior surface having a complementary rounded recess. The 25 discrete base members can be fashioned to meet different clinical conditions and/or optionally provide additional positive Diopter power if so required.

SUMMARY OF THE INVENTION

The present invention is directed towards accommodating intraocular lens (AIOL) capsules having a generally disc shaped resiliently elastically compressible shape memory construction with a continuously variable Diopter strength between a first preferably zero Diopter strength in a non-compressed state and a second Diopter strength different than its first Diopter strength in a compressed state on application of an axial compression force from a posterior 5 direction. The AIOL capsules include a capsule housing having an anterior capsule plate, a posterior capsule plate,' and a capsule ring for bounding a hermetic cavity filled with a transparent capsule filling constituted by either a gel or a liquid having a higher refractive index than the human eye's aqueous humour. The anterior and posterior capsule plates are preferably made from biocompatible transparent plastic material having a hardness rating on the Shore range A from between about 20 and about 80. Suitable gels have a hardness rating below the measurement range of the Shore scale, namely, less than measurable on the Shore 00 range and therefore measured in a penetration test using a penetrometer. AIOL capsules can be implemented with one or more of several features for facilitating their intended anterior bulging under the relative small compression forces developed by a human eye.

AIOL capsules are preferably provisioned as unitary AIOLs similar to aforesaid PCT International Publication No. WO 2008/107882 with an integrally formed rigid haptics system having a pair of diametrically opposite elongated generally C-shaped haptics for self-anchoring in a human eye's ciliary sulcus. Alternatively, AIOL capsules can be discrete units for in situ assembly with a haptics system in a human eye thereby enabling their insertion into a human eye through a smaller incision than in the case of unitary AIOL.

AIOL capsules can be fashioned for use with either a purpose designed discrete H-shaped base member or a previously implanted standard in-the-bag IOL in a similar manner to aforesaid PCT International Publication No. WO 2008/107882. In the latter case, an intermediate ciliary sulcus fixed Diopter strength intraocular lens may be implanted between the standard in-the-bag IOL and an AIOL capsule of the present invention. AIOL assemblies can be designed with zero Diopter strength or positive Diopter strength in a non-compressed state to satisfy a particular clinical condition. Positive Diopter strengths can be afforded either by a discrete base member or an AIOL capsule having a posterior capsule plate with a convex trailing surface. In the latter case, such AIOL capsules can be implanted with a washer-like base member having a throughgoing aperture through which an AIOL capsule's convex trailing surface extends therethrough for direct contact with a human eye's capsular diaphragm. The H-shaped base member and the washer-like base member can also be employed for use with unitary AIOLs as disclosed in aforesaid PCT International Publication No. WO 2008/107882.

The haptics systems preferably include a Vertical Adjustment Mechanism (VAM) including a biocompatible energy absorbing U-shaped clip on each haptics with a crosspiece facing in an anterior direction on implantation of an AIOL assembly in a human eye. The clips are preferably protected by biocompatible silicon gel for thermal protection. The clips are optionally covered by biocompatible black carbon applied using liquid silicone which dries.

The haptics systems preferably include an attachment plate similar to the aforesaid PCT International Publication No. WO 2006/103674's attachment plate except the present invention's attachment plate includes a pair of side-by-side manipulation holes as opposed to a single manipulation hole. The side-by-side manipulation holes facilitate the simultaneous use of two different handheld implantation tools for implanting an AIOL assembly in a human eye.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE PRESENT INVENTION

Figure 1:
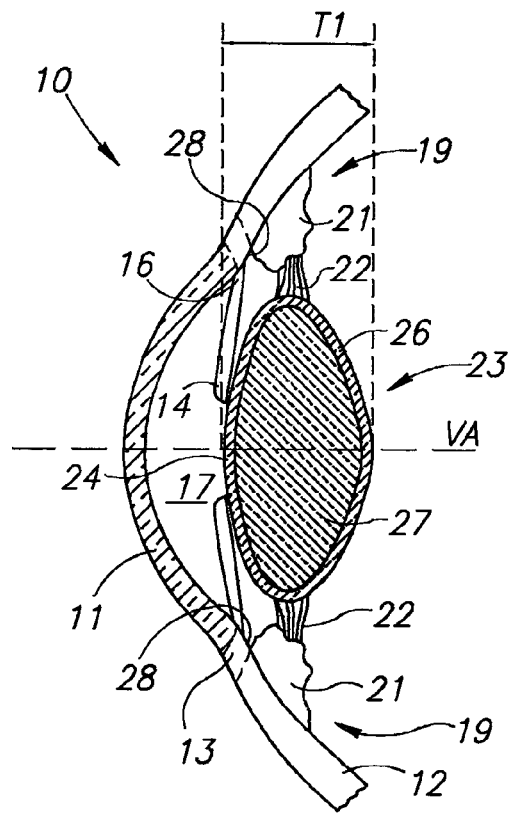
FIG. 1 is a cross section view of an anterior part of a human eye in its contracted ciliary body state for natural near vision in an axial plane of the human body.
Figure 2:
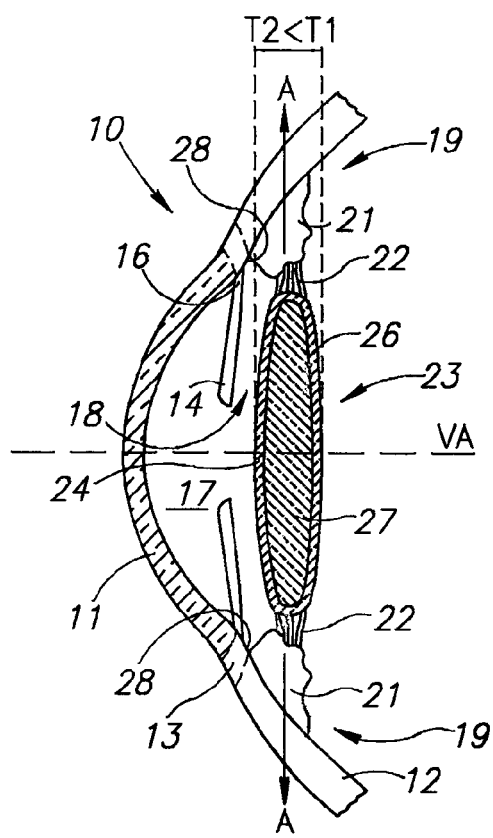
FIG. 2 is a cross section view of an anterior part of a human eye in its relaxed ciliary body state for natural distance vision in an axial plane of the human body.

FIGS. 1 and 2 are cross section views of an anterior part of a human eye having a visual axis VA in its natural near and distance vision conditions, respectively, in an axial plane of the human body. The human eye 10 has a cornea 11 peripherally connected to a spherical exterior body made of tough connective tissue known as the sclera 12 at an annular sclero-corneal juncture 13. An iris 14 inwardly extends into the human eye 10 from its root 16 at the sclero-corneal juncture 13 to divide the human eye's anterior part into an anterior chamber 17 and a posterior chamber 18. A sphincter-like peripheral structure known as the ciliary body 19 includes ciliary processes housing ciliary muscles 21 fired by parasympathetic nerves. The ciliary muscles 21 are connected to zonular fibers 22 which in turn are peripherally connected to the equatorial edge of a membrane known as the capsular bag 23 with an anterior capsule 24 and a posterior capsule 26 enrobing a natural crystalline lens 27. The iris's root 16 and 15 the ciliary body 19 delimit a portion of the interior surface of the sclera 12 at the sclero-corneal juncture 13 known as the ciliary sulcus 28. Remnants of the anterior capsule 24 which may remain after extraction of the natural crystalline lens 27 and the intact posterior capsule 26 are referred to hereinafter as the capsular diaphragm 29. Contraction of the ciliary body 19 allows the lens 27 to thicken to its natural thickness T1 along the visual axis VA for greater positive optical power for near vision (see FIG. 1). Relaxation of the ciliary body 19 tensions the zonular fibers 22 which draws the capsular bag 23 radially outward as shown by arrows A for compressing the lens 27 to shorten its thickness along the visual axis VA to T2<T1 for lower positive optical power for distance vision (see FIG. 2).

Figure 3:
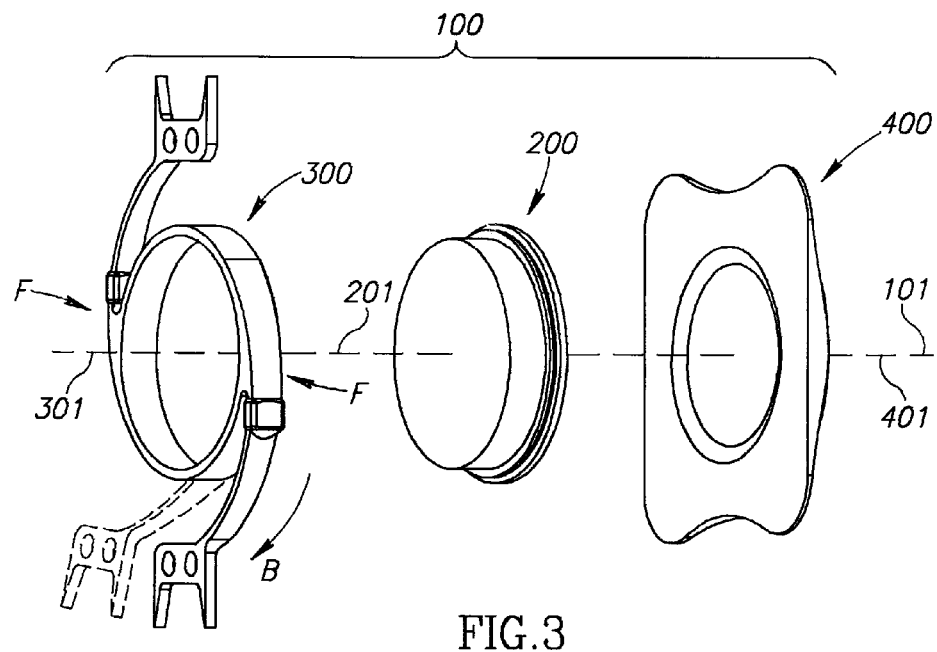
FIG. 3 is an exploded view of an AIOL assembly including a haptics system, an AIOL capsule and a purpose designed H-shaped base member.
Figure 4:
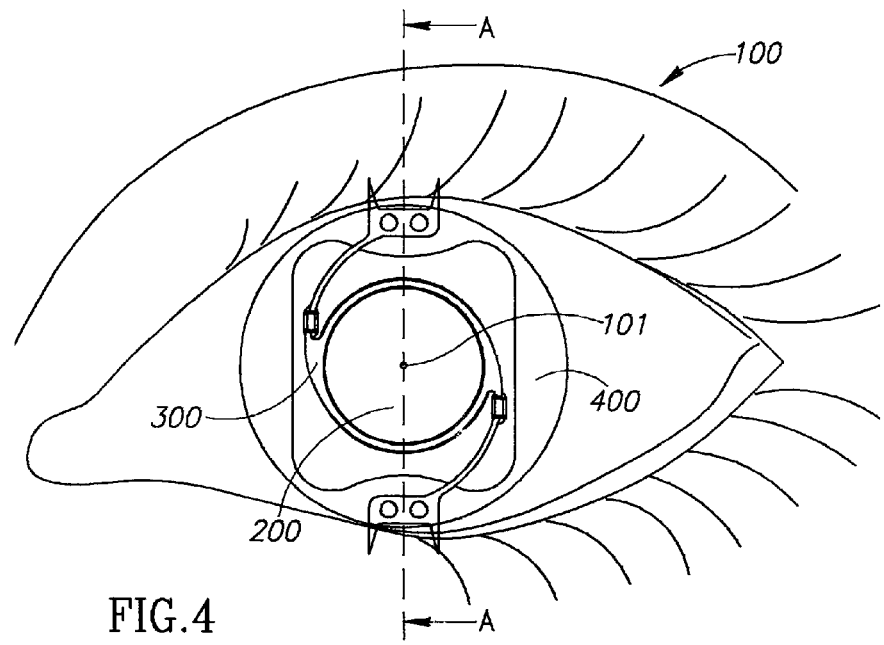
FIG. 4 is a front view of a human eye including FIG. 3's AIOL assembly implanted therein.
Figure 5:
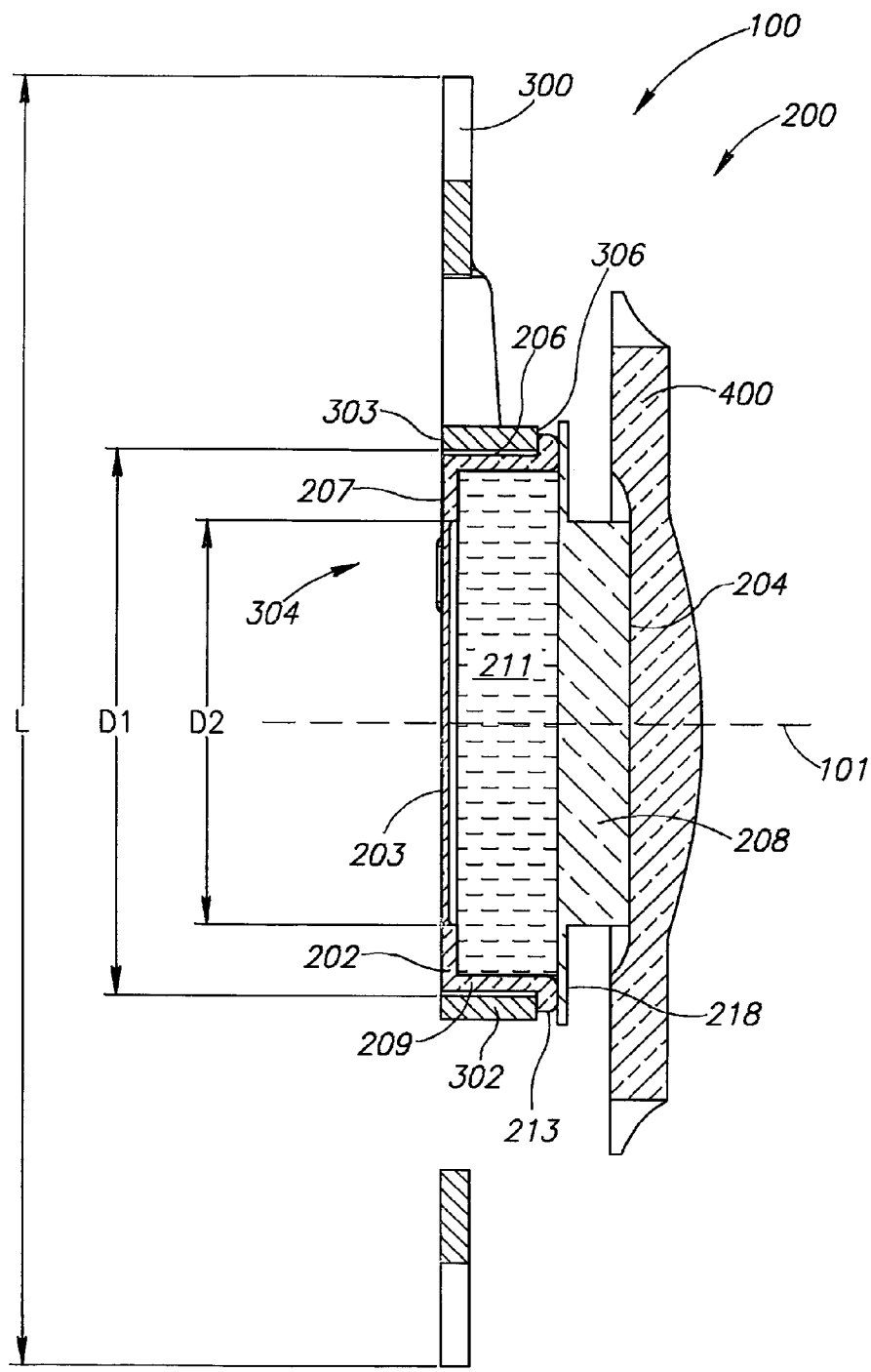
FIG. 5 is a longitudinal cross section of FIG. 3's haptics system and AIOL capsule in a non-compressed state along line A-A in FIG. 4.

FIGS. 3 to 5 show an AIOL assembly 100 including an AIOL capsule 200 for use with a haptics system 300 for self-anchoring in a human eye's ciliary sulcus 28 and a purpose designed discrete H-shaped base member 400 interposed between the AIOL capsule 200 and a human eye's capsular bag 23 for transferring an axial compression force therefrom to the AIOL capsule 200. Alternatively, the AIOL capsule 200 can be used with a standard previously implanted in-the-bag IOL. The AIOL assembly 100 has a longitudinal axis 101 intended to be co-directional and preferably co-axial with a human eye's visual axis VA on implantation in a human eye 10. The AIOL capsule 200 and the haptics system 300 are preferably pre-assembled using conventional assembly techniques, for example, gluing, soldering, and the like.

The AIOL capsule 200 includes a longitudinal axis 201 intended to be co-axial with the AIOL assembly's longitudinal axis 101 on implantation of the AIOL assembly 100 in a human eye. The AIOL capsule 200 has a generally disc shaped resiliently elastically compressible shape memory construction. The AIOL capsule 200 includes a capsule housing 202 having an exposed leading surface 203, an exposed trailing surface 204 opposite and parallel to the leading surface 203, and a peripheral surface 206 extending between the leading and trailing surfaces 203 and 204. The capsule housing 202 is intended to anteriorly bulge along the human eye's visual axis VA on application of an axial compression force against the trailing surface 204 from a posterior direction. The AIOL capsule 200 has a continuously variable Diopter strength between a first preferably zero Diopter strength in a non-compressed state (see FIG. 6) and a second Diopter strength different than its first Diopter strength in a compressed state (see FIG. 7) on application of the axial compression force as indicated by arrows C in FIG. 6.

FIGS. 3 to 5 show the haptics system 300 includes a longitudinal axis 301 intended to be co-axial with the AIOL assembly's longitudinal axis 101 on implantation of the AIOL assembly 100 in a human eye. The haptics system 300 has a haptics length L and includes a tubular haptics main body 302 with a haptics external diameter D1. Exemplary dimensions of the haptics length L are 11 to 14 mm and the haptics main body external diameter D1 are 5 to 7 mm. The 30 haptics main body 302 has a leading end face 303 defining a preferably circular aperture 304 through which the AIOL capsule 200 anteriorly bulges therethrough on application of an axial compression force from a posterior direction, and an opposite trailing end face 306. The haptics main body 302 is preferably designed to be squeezable on application of a pincer-like compression force denoted F in FIG. 3 such that they temporarily and reversibly assume an elliptic shape to reduce their width for lengthwise insertion into a small corneal incision to assist implantation. The haptics system 300 is made from suitable rigid biocompatible transparent polymer material such as PMMA, and the like.

FIGS. 3 and 8 to 11 show the haptics system 300 includes a pair of diametrically opposite elongated generally C-shaped haptics 307 extending in opposite directions in a plane perpendicular to the longitudinal axis 301. The haptics 307 have a thin profile in the plane perpendicular to the longitudinal axis 301 such that they are sufficiently flexible under reasonable forces as can be applied using conventional ophthalmic surgical tools for encircling around the haptics main body 302 denoted by arrow B in FIG. 3 for facilitating insertion into a human eye through a relatively small incision. FIG. 3 shows a haptics 307 in dashed lines for showing its encircling around the haptics main body 302. The haptics 307 have a wide profile along the longitudinal axis 301 such that they are rigid against a compression force therealong. The haptics' wide profile preferably tapers from its proximal end 307A adjacent the haptics main body 302 to its distal end 307B remote therefrom and terminating at a bifurcated attachment plate 308.

The attachment plates 308 include a pair of spaced apart puncturing members 309 having tips 311 with a minimum tip separation TS of at least 1 mm and preferably between about 2 mm and 3 mm and a minimum tip height TH of at least 0.5 mm such that they can penetrate slightly more than half of a sclera's thickness of about 1 mm thereby providing the AIOL assembly 100's anchoring points. The attachment plates 308 include a pair of side-by-side manipulation holes 312 for facilitating the simultaneous use of two different handheld 30 implantation tools for implanting an AIOL assembly in a human eye. The manipulation holes 312 preferably have a minimum manipulation hole separation MHS between their centers of about 1.5 mm and a diameter of about 0.5 mm.

Each haptics 307 includes a Vertical Adjustment Mechanism (VAM) 320 for enabling in situ longitudinal displacement of a haptics main body 302 relative to the AIOL assembly 100's anchoring points along a visual axis VA thereby, controlling the position of the haptics main body 302 relative to an eye's capsular diaphragm 29. The VAMs 320 enable in situ correction of the placement of the AIOL assembly 100 in case it is placed too posterior or alternatively in case of excessive pressure being developed by an eye's capsular diaphragm. The VAMs 320 include the provision of each haptics 307 with a heat deformable region 321 adjacent the haptics main body 302 and intended to undergo local heating by an external energy source.

Each VAM 320 includes an energy absorbent U-shaped clip 322 for clipping onto its respective haptics 307 adjacent the haptics main body 302. The U-shaped clips 322 have a cross piece 323 extending between a pair of opposite legs 324. The clips 322 are intended to be clipped onto their respective haptics 307 such that their respective cross pieces 323 are anteriorly directed. The clips 322 are preferably formed from a low specific heat metal, for example, titanium, and the like. The clips 322 are preferably covered by biocompatible black carbon 326 applied using liquid silicone which dries. The black carbon 326 is in turn preferably covered by biocompatible silicon gel 327 for thermal protection. The clips 322 are intended to be irradiated with suitable laser light, for example, for retinal photocoagulation, laser trabeculopasty, and the like, for enabling localized heating of their respective heat deformable regions 321 to a temperature higher than a human eye's normal 36° C. temperature but sufficiently low so as not to damage a human eye's delicate internal structures. Suitable laser systems include inter alia the Oculight SL 810 nm Infrared Photocoagulator commercially available from IRIDEX Corporation, California, USA www.iridex.com.

Figures 6, 7:
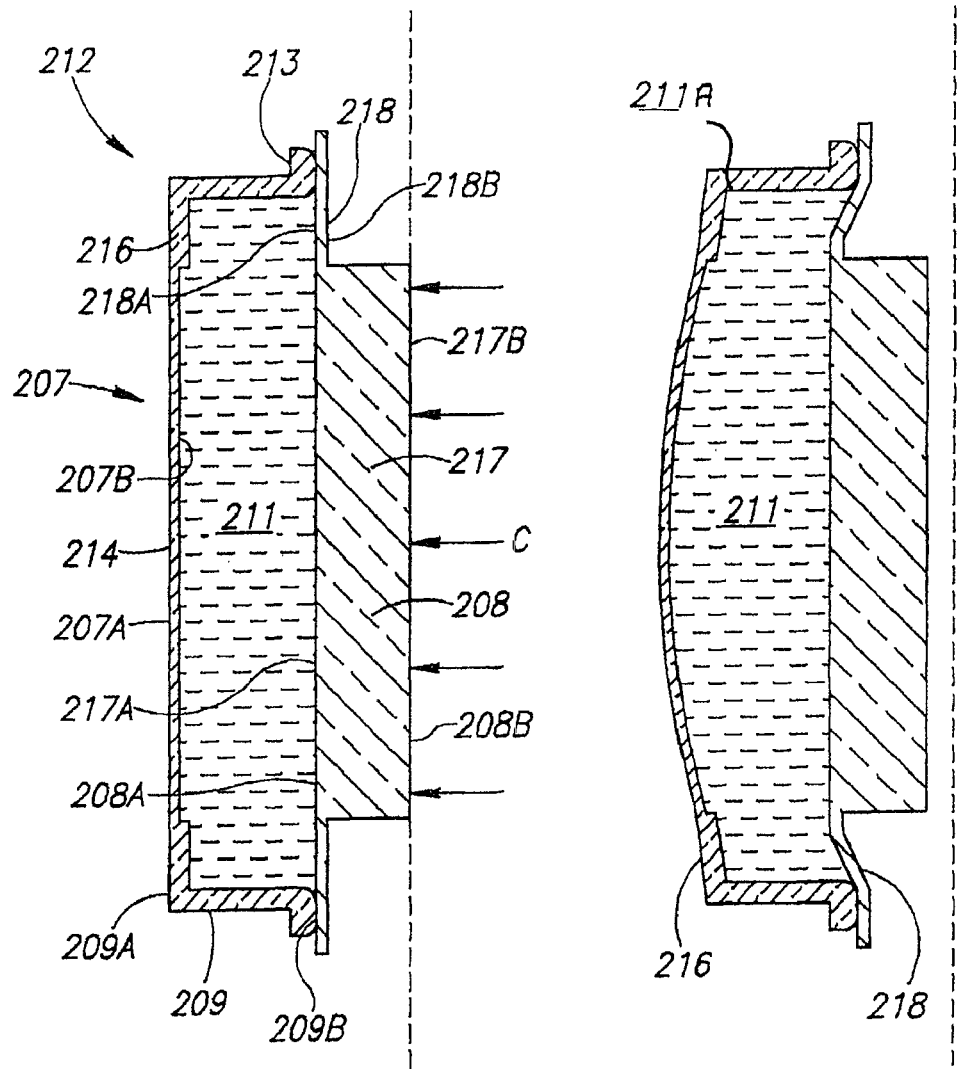
FIG. 6 is a longitudinal cross section of FIG. 3's AIOL capsule in a non-compressed state along line A-A in FIG. 4.
FIG. 7 is a longitudinal cross section of FIG. 3's AIOL capsule in a compressed state along line A-A in FIG. 4.
Figure 8:
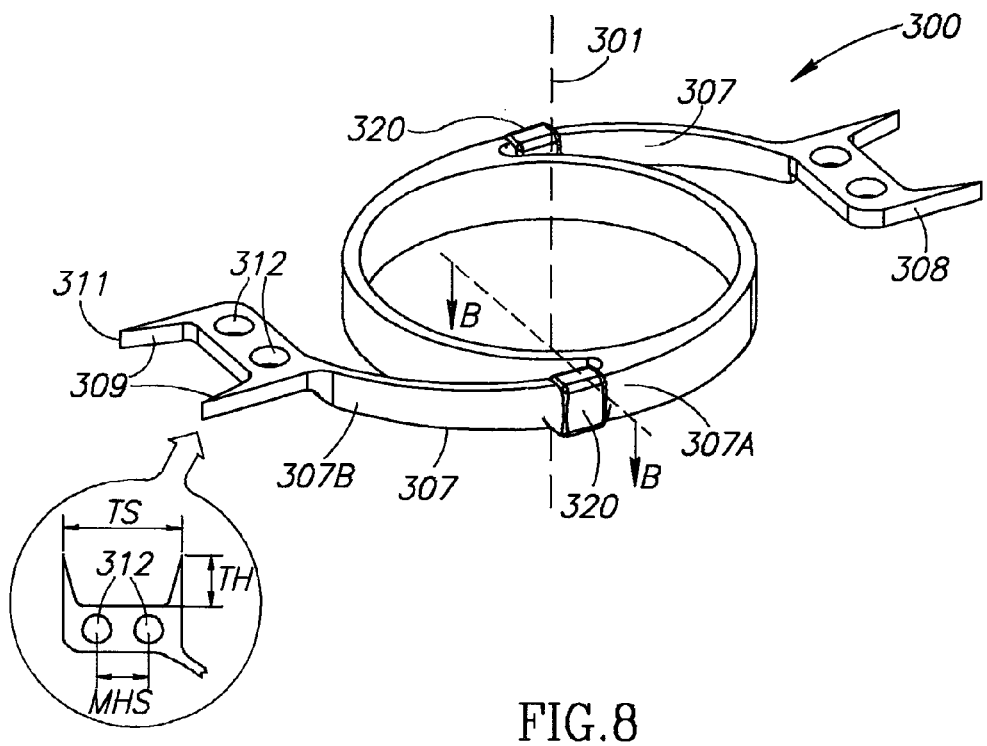
FIG. 8 is a front perspective view of a haptics system with their each haptic incorporating a VAM in accordance with the present invention.
Figure 9:
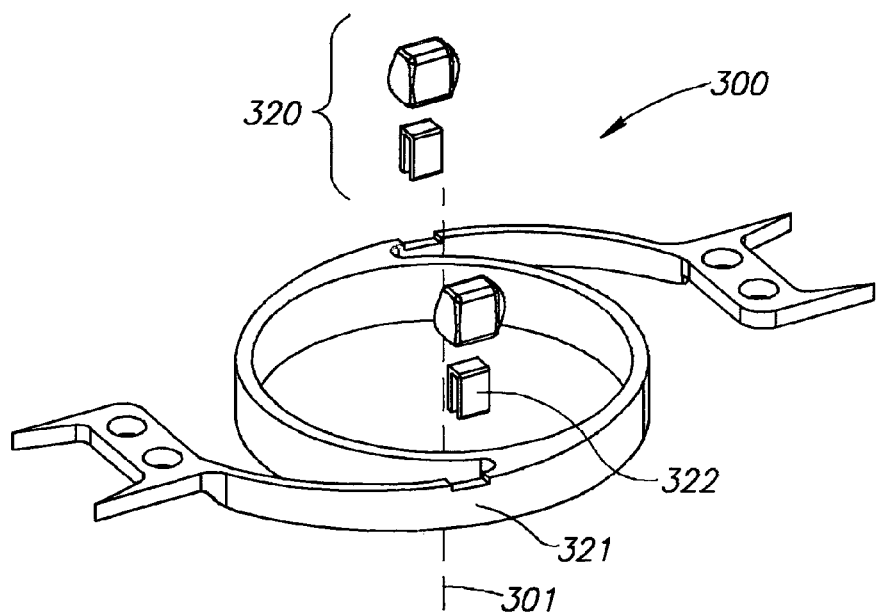
FIG. 9 is an exploded view of a VAM.
Figure 10:
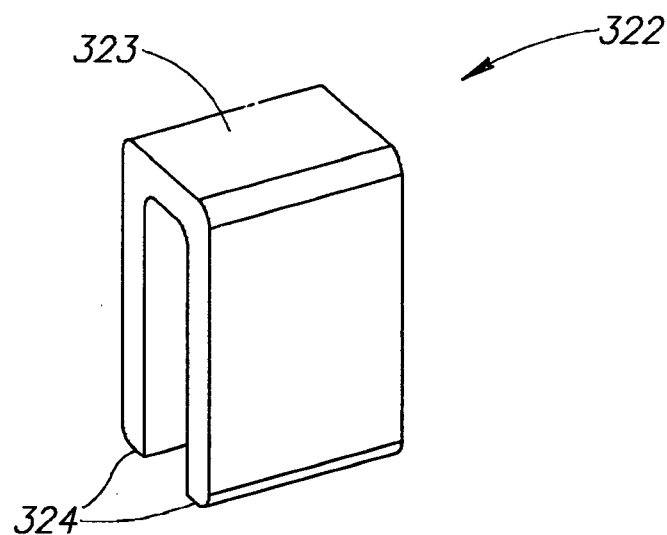
FIG. 10 is an enlarged front perspective view of a VAM's U-shaped clip.
Figure 11:
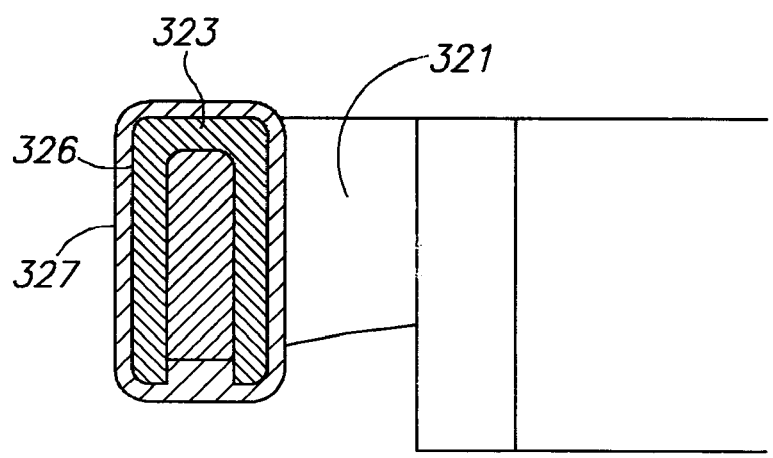
FIG. 11 is a cross section of a VAM along line B-B in FIG. 8.

FIGS. 5 to 7 show the capsule housing 202 includes a generally circular 30 anterior capsule plate 207 with an exposed leading surface 207A and a concealed trailing surface 207B, a posterior capsule plate 208 including a concealed leading surface 208A and an exposed trailing surface 208B, and a capsule ring 209 extending between the anterior and posterior capsule plates 207 and 208 and having opposite leading and trailing rims 209A and 209B. The capsule ring's leading rim 209A meets the anterior capsule plate 207 and its trailing rim 209B meets the posterior capsule plate 208. The leading surface 207A constitutes the AIOL capsule's exposed leading surface 203, the trailing surface 208B constitutes the AIOL capsule's exposed trailing surface 204, and the capsule ring 209 constitutes the AIOL capsule's peripheral surface 206. The anterior capsule plate 207, a posterior capsule plate 208 and the capsule ring 209 bound a hermetic cavity 211. The anterior capsule plate 207 and the capsule ring 209 meet at a right angle affording the hermetic cavity 211 with a sharp leading rim 211A.

The anterior capsule plate 207, the posterior capsule plate 208 and the capsule ring 209 are formed from biocompatible transparent polymer material.

Suitable polymer materials are preferably silicon based and have a hardness rating on Shore range A between about 20 and about 80. Suitable silicon based polymer materials are commercially available from NuSil Technology LLC., US (www.nusil.com). The cavity 211 is filled with a biocompatible transparent capsule filling constituted by a gel or liquid. Suitable gels are preferably silicon based and have a hardness rating below the measurement range of Shore 00 and therefore only measurable in a penetration test using a penetrometer. Suitable silicon based gels are commercially available from NuSil Technology LLC., US (www.nusil.com).

The anterior capsule plate 207 and the capsule ring 209 are preferably manufactured as a single monolithic bowl-like capsule shell 212 on which the posterior capsule plate 208 is rear sided mounted for sealing the cavity 211. The trailing rim 209B preferably extends outward to provide an annular flange 213 for abutting against the haptics main body's trailing end face 306 on assembly of the AIOL capsule 200 and the haptics system 300. The anterior capsule plate 207 preferably includes an inner thin circular region 214 intended to undergo anterior bulging and a thicker support ring 216 connected to the capsule ring's leading rim 209A. The thin circular region 214 which acts as the AIOL capsule's main optical aperture has a diameter D2 in the region of 3.5 to 5.5 mm. The thin circular region 214 has a thickness typically in the range of 20 to 60 um.

The posterior capsule plate 208 includes a central capsule filling displacement member 217 with a peripheral annular flange 218 intended to be rear side mounted on the annular flange 213. The capsule filling displacement member 217 and the flange 218 respectively have leading surfaces 217A and 218A constituting the posterior capsule plate's leading surface 208A. The capsule filling displacement member 217 and the peripheral annular flange 218 respectively have trailing surfaces 217B and 218B constituting the posterior capsule plate's trailing surface 208B. The flange 218 is capable of undergoing repeated back and forth flexing to enable reciprocation of the capsule filling displacement member 217 with respect to the capsule ring 209 for causing repeated anterior bulging. The capsule filling displacement member 217 and the flange 218 have co-planar leading surfaces 217A and 218A in the AIOL capsule's non-compressed state in the absence of the axial compression force C (see FIG. 6). The posterior capsule plate 208 has a stepped trailing surface 208B with the capsule filling displacement member's trailing surface 217B protruding posteriorly with respect to the flange's trailing surface 218B. The capsule filling displacement member's trailing surface 217B acts as the AIOL capsule's trailing surface 204 in terms of the axial compression force being applied thereagainst. FIG. 7 shows the support ring 216's and the flange 218's anterior flexing from their non-flexed positions on application of the axial compression force C against the capsule filling displacement member's trailing surface 217B as exemplified by the separation of the capsule filling displacement member's trailing surface 217B from the dashed reference line.

Figure 12:
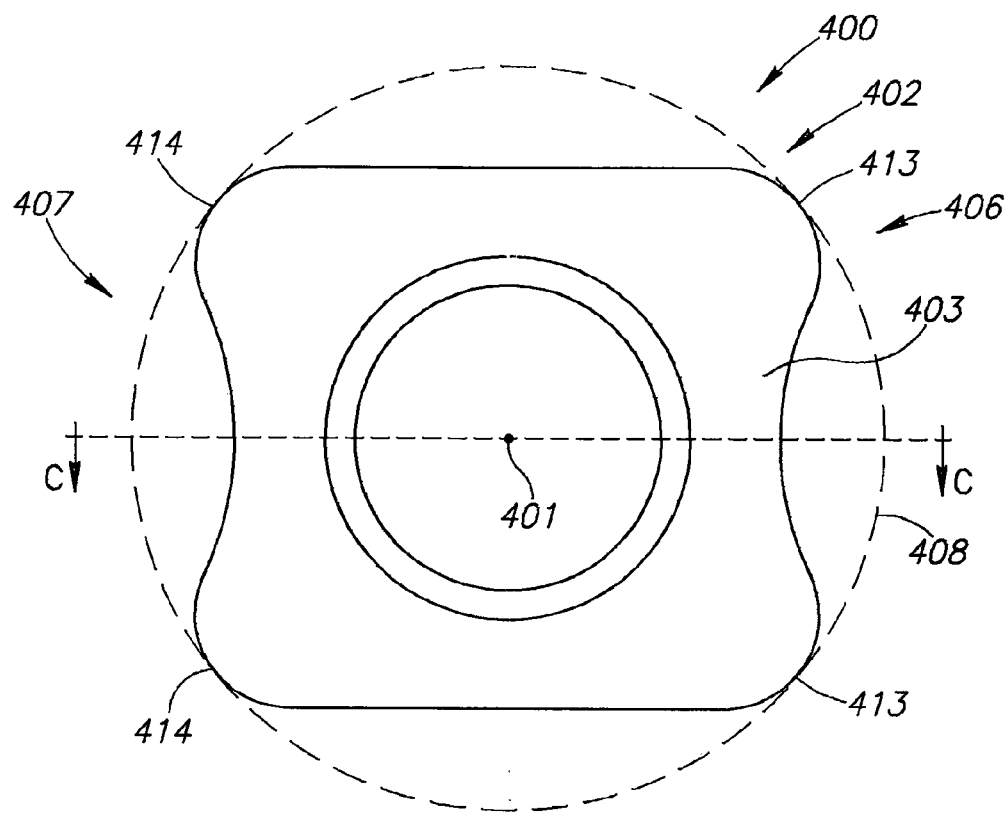
FIG. 12 is a plan view of FIG. 3's H-shaped base member.
Figure 13:
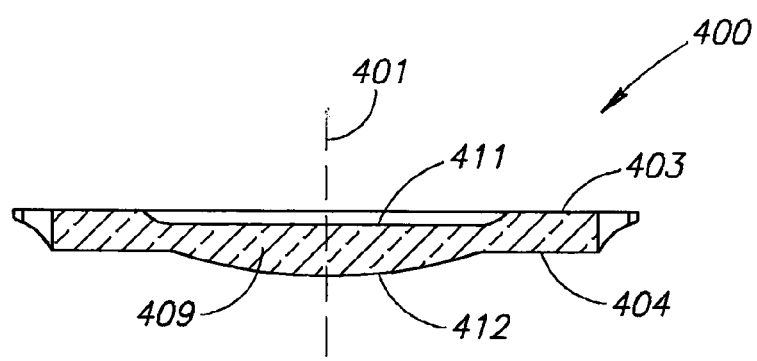
FIG. 13 is a cross section of FIG. 3's H-shaped base member along line C-C in FIG. 12.

FIGS. 12 and 13 show the base member 400 having a longitudinal axis 401 intended to be co-axial with the AIOL assembly's longitudinal axis 101 on 30 implantation in a human eye. The base member 400 has an elongated substantially planar main body 402 with opposite major anterior and posterior surfaces 403 and 404. The base member 400 is preferably made from pliable biocompatible transparent polymer material for enabling folding for insertion through a small incision into a human eye and conform to the natural curvature of a human eye's capsular diaphragm on implantation in a human eye. Suitable polymer materials include inter alia HydroxyEthylMethaAcrylate (HEMA), and the like.

The main body 402 has opposite leading and trailing ends 406 and 407 which define an imaginary circle 408 having an about 13 to 15 mm diameter which is sufficient to conform to the natural curvature of a human eye's capsular diaphragm and extend into substantially opposite locations of a human eye's ciliary sulcus 28. The main body 402 has a central piston member 409 co-axial with the longitudinal axis 401. The central piston member 409 has leading and trailing working surfaces 411 and 412. The leading working surface 411 is preferably depressed with respect to the surrounding major anterior surface 403 thereby effectively rendering a generally circular depression for receiving the capsule filling displacement member's trailing surface 217B thereby ensuring correct alignment between the AIOL capsule 200 and the base member 400. The trailing working surface 412 is preferably convex for affording up to about 18 Diopter strength. The leading end 406 has a first pair of spaced apart lateral wings 413 and the trailing end 407 has an opposite pair of spaced apart lateral wings 414 extending radial from the piston member 409 thereby affording an overall H-shape to the base member 400 in FIG. 12's top view.

Figure 14:
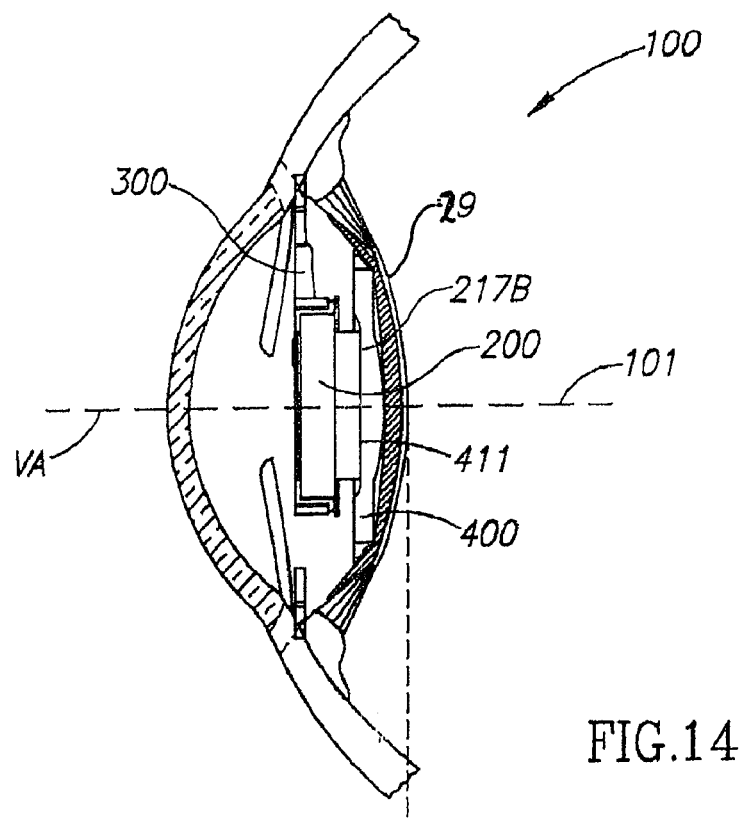
FIG. 14 is a longitudinal cross section of an anterior part of a human eye showing deployment of FIG. 3's AIOL assembly in an axial plane of the human eye in the eye's contracted ciliary body state.
Figure 15:
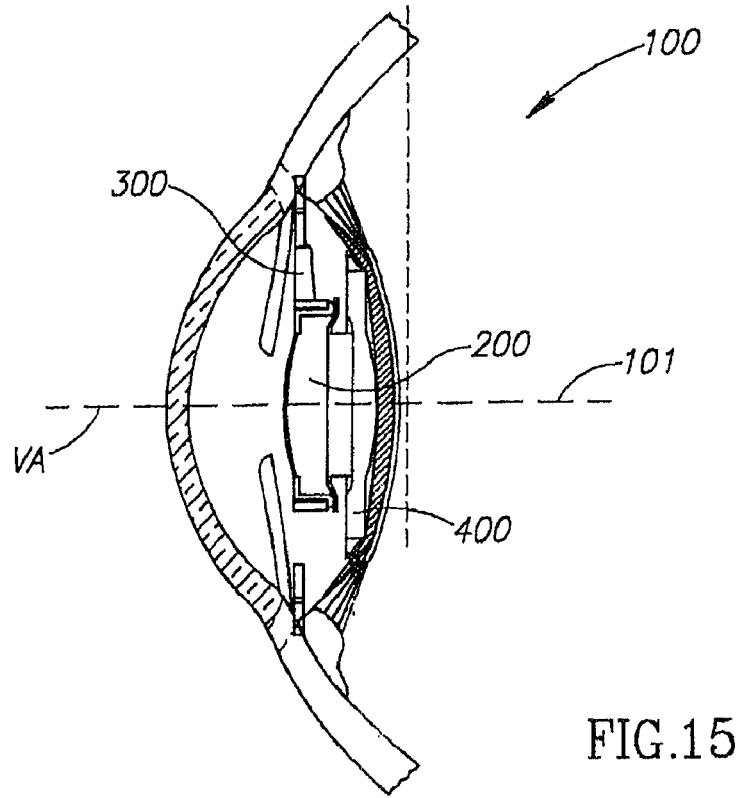
FIG. 15 is a longitudinal cross section of an anterior part of a human eye showing deployment of FIG. 3's AIOL assembly in an axial plane of the human eye in the eye's relaxed ciliary body state.

FIGS. 14 and 15 show implantation of the AIOL assembly 100 in a human eye and its operation between its non-compressed state in the eye's contracted ciliary body state and its compressed state and in the eye's relaxed ciliary body state, respectfully.

Figure 16:
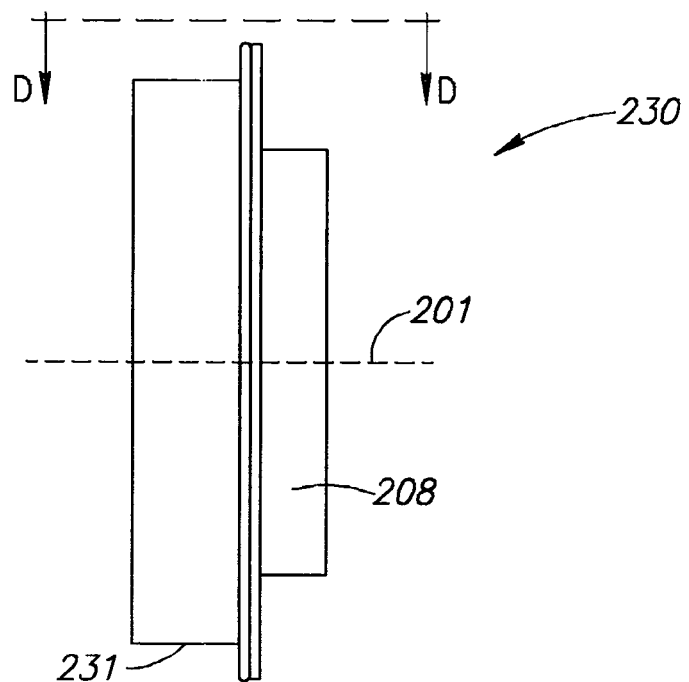
FIG. 16 is a side view of an AIOL capsule having a capsule shell with a filleted leading internal surface according to another embodiment of the present invention.
Figure 17:
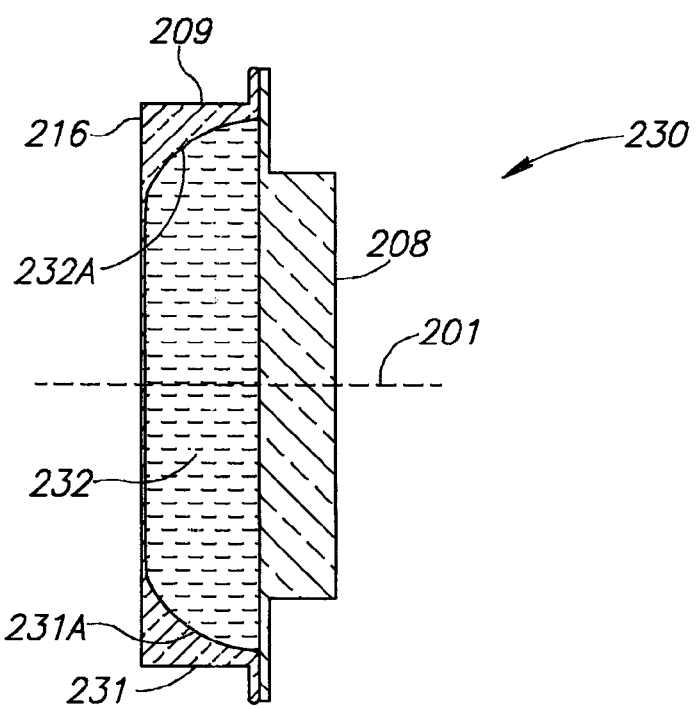
FIG. 17 is a cross section of FIG. 16's AIOL capsule along line D-D in FIG. 16.

FIGS. 16 and 17 show an AIOL capsule 230 similar in construction to the AIOL capsule 200 and therefore similar parts are likewise numbered. The AIOL capsule 230 is also intended for use with the H-shaped base member 400.

The AIOL capsule 230 includes a capsule shell 231 for bounding a hermetic cavity 232 sealed by the posterior capsule plate 208. The capsule shell 231 has a filleted leading internal surface 231A affording the hermetic cavity 232 with a rounded leading rim 232A adjacent the anterior capsule plate 207 for assisting anterior bulging.

Figure 18:
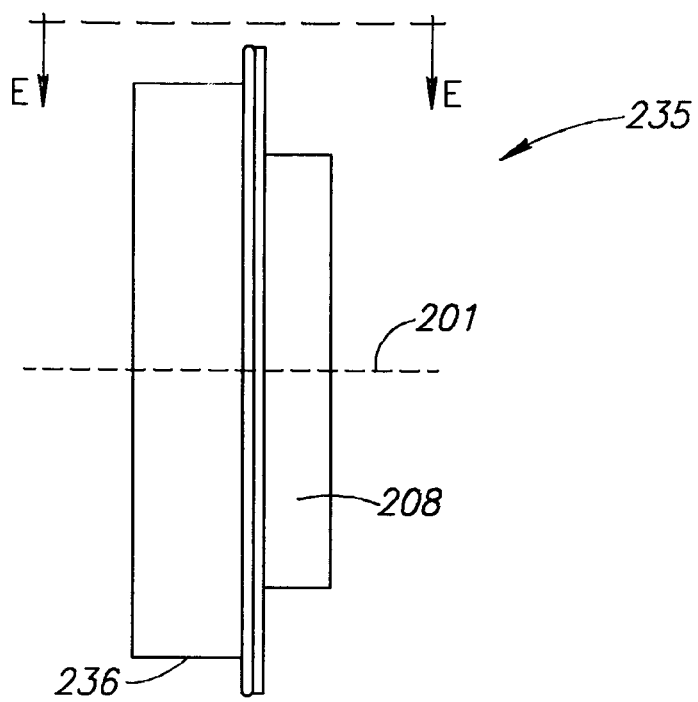
FIG. 18 is a side view of an AIOL capsule having a capsule shell with a cone section shaped hermetic cavity converging in an anterior direction along its longitudinal axis according to another embodiment of the present invention.
Figure 19:
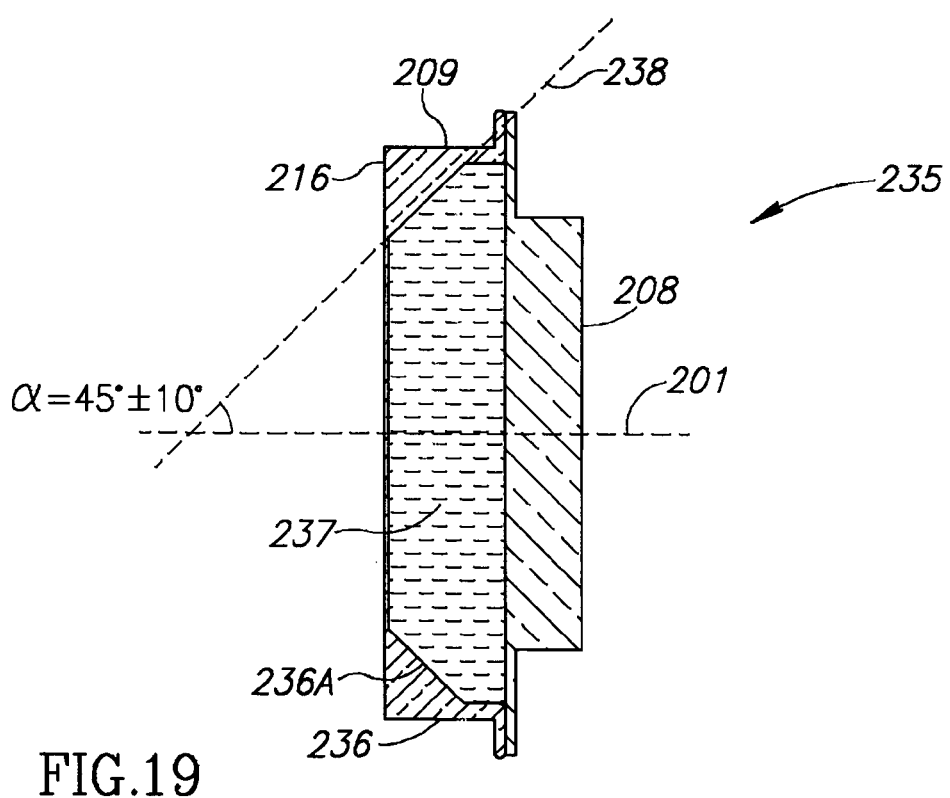
FIG. 19 is a cross section of FIG. 18's AIOL capsule along line E-E in FIG. 18.

FIGS. 18 and 19 show an AIOL capsule 235 similar in construction to the AIOL capsule 200 and therefore similar parts are likewise numbered. The AIOL capsule 235 is also intended for use with the H-shaped base member 400. The AIOL capsule 235 includes a capsule shell 236 for bounding a hermetic cavity 237 sealed by the posterior capsule plate 208. The capsule shell 236 has an angled leading internal surface 236A for affording the hermetic cavity 237 with a cone section shape converging in an anterior direction along the longitudinal axis 201. The hermetic cavity 237 has a generatrix 238 defining an angle a=45°±10° with the longitudinal axis 201.

Figure 20:
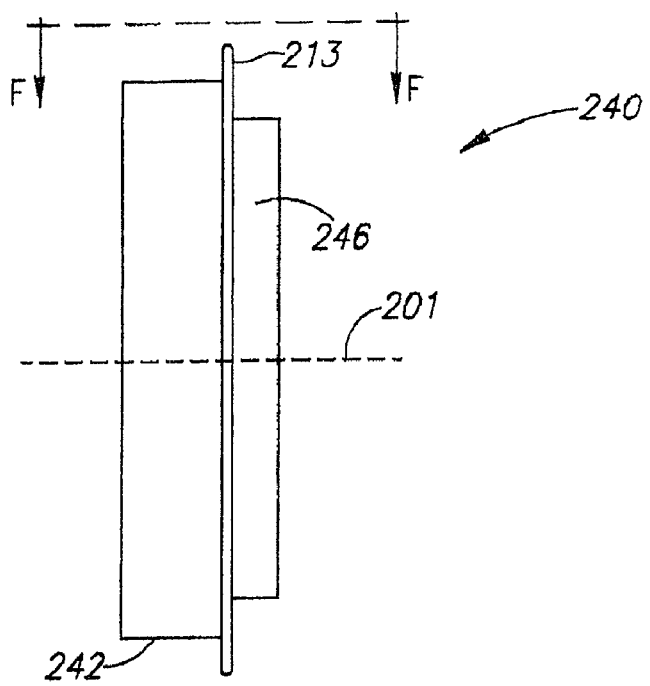
FIG. 20 is a side view of an AIOL capsule having a capsule shell with a cone section shaped hermetic cavity converging in a posterior direction along its longitudinal axis according to another embodiment of the present invention.
Figure 21:
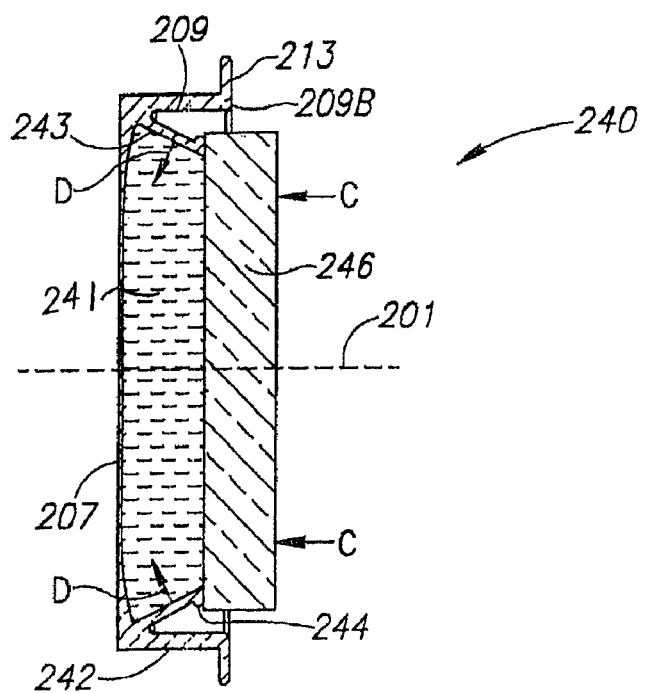
FIG. 21 is a cross section of FIG. 20's AIOL capsule along line F-F in FIG. 20.

FIGS. 20 and 21 show an AIOL; capsule 240 similar in construction to the AIOL capsule 200 and therefore similar parts are likewise numbered. The AIOL capsule 240 is also intended for use with the H-shaped base member 400. The AIOL capsule 240 differs from the AIOL capsule 200 insofar that AIOL capsule 240 includes a hermetic cavity 241 with a cone section shape converging in a posterior direction along the longitudinal axis 201 for assisting anterior bulging. This cavity construction is achieved by the AIOL capsule 240 including a capsule shell 242 with an additional converging tubular wall 243 extending from the juncture between its anterior capsule plate 207 and capsule ring 209. The converging tubular wall 243 terminates at a trailing rim 244 recessed with respect to the capsule ring's trailing rim 209B along the longitudinal axis 201. A disc-like posterior capsule plate 246 is rear mounted on the trailing rim 244 rather than on the annular flange 213 and extends in a posterior direction beyond the capsule ring's trailing rim 209B along the longitudinal axis 201. The converging tubular wall 243 is intended to bulge inwards towards the longitudinal axis 201 as shown by arrows D on application of the axial compression force C for assisting anterior bulging.

Figure 22:
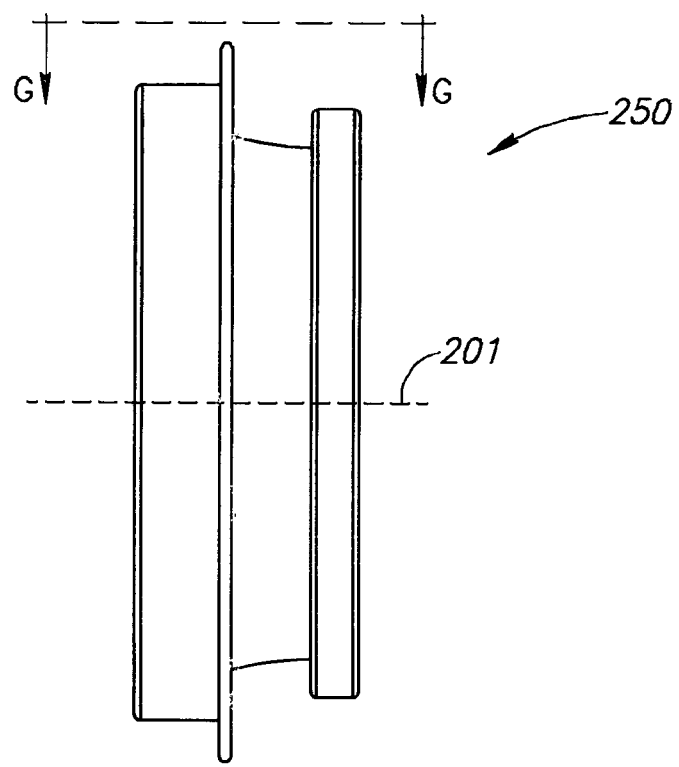
FIG. 22 is a side view of a variation of FIG. 20's AIOL capsule.
Figure 23:
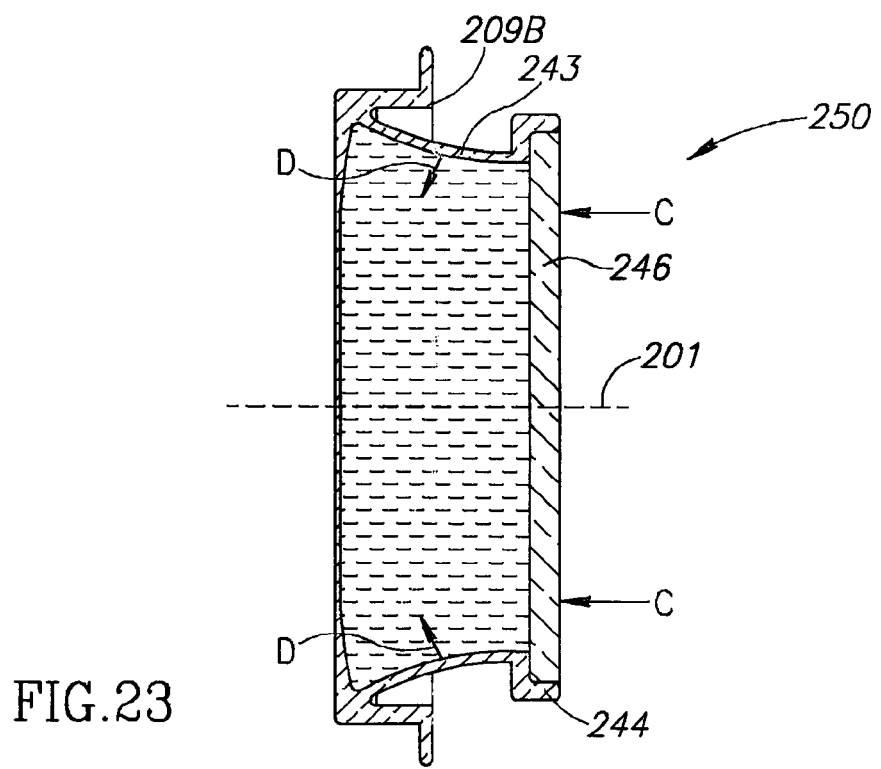
FIG. 23 is a cross section of FIG. 22's AIOL capsule along line G-G in FIG. 22.

FIGS. 22 and 23 show an AIOL capsule 250 similar in construction to the AIOL capsule 240 and therefore similar parts are likewise numbered. The AIOL capsule 250 is also intended for use with the H-shaped base member 400. The AIOL capsule 250 differs from the AIOL capsule 240 insofar the former's converging tubular wall 243's trailing rim 244 protrudes beyond the capsule ring's trailing rim 209B in a posterior direction along the longitudinal axis 201. A thin disc-like posterior capsule plate 246 is mounted on the trailing rim 244.

The converging tubular wall 243 is intended to bulge inwards towards the longitudinal axis 201 as shown by arrows D on application of the axial compression force C for assisting anterior bulging.

Figure 24:
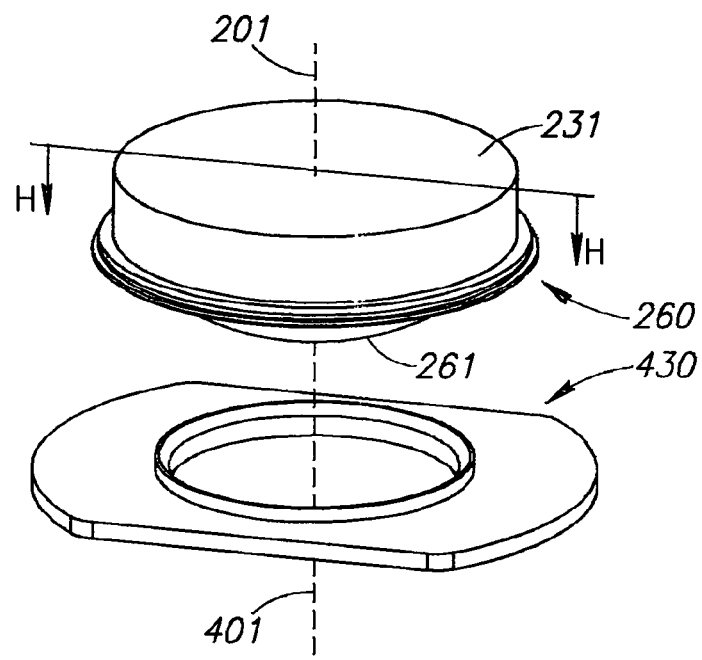
FIG. 24 is a perspective view of FIG. 16's capsule shell with an alternative posterior capsule plate and a washer-like base member for use therewith.
Figure 25:
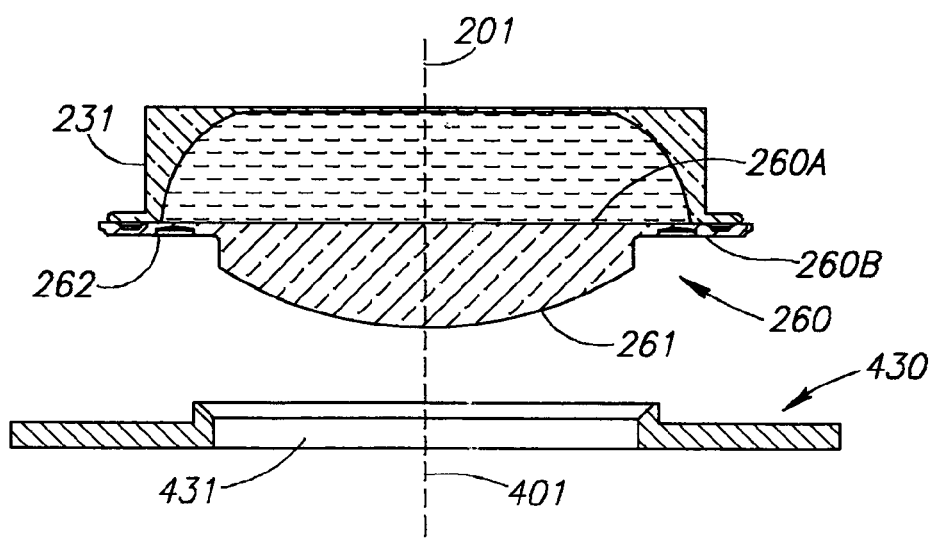
FIG. 25 is a cross section of FIG. 24's capsule shell and washer-like base 20 member along line H-H in FIG. 24.
Figure 26:
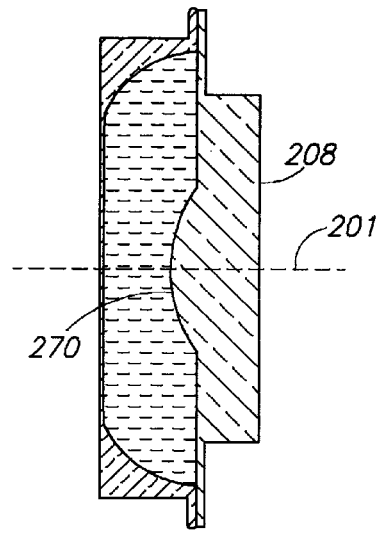
FIG. 26 is a cross section of FIG. 16's AIOL capsule with its posterior capsule plate formed with a bulge control element.
Figure 27:
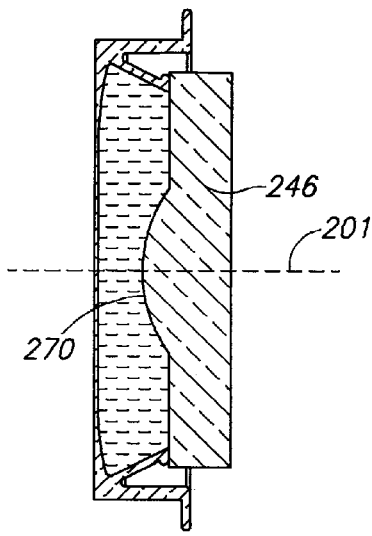
FIG. 27 is a cross section of FIG. 20's AIOL capsule with its posterior capsule plate formed with a bulge control element.
Figure 28:
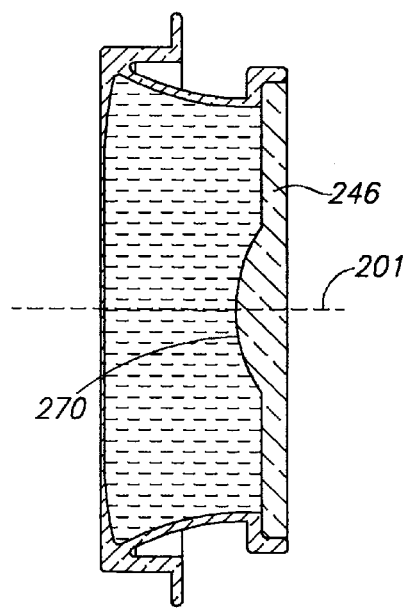
FIG. 28 is a cross section of FIG. 22's AIOL capsule with its posterior capsule plate formed with a bulge control element.
Figure 29:
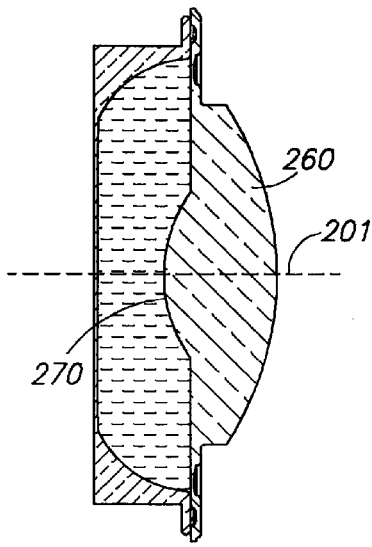
FIG. 29 is a cross section of FIG. 24's AIOL capsule with its posterior capsule plate formed with a bulge control element.

FIGS. 24 and 25 show the capsule shell 231 with a posterior capsule plate 260 and a washer-like base member 430 for use therewith instead of the base member 400. The posterior capsule plate 260 includes a leading surface 260A for rear side mounting on the capsule shell 231 and a trailing surface 260B including a central convex surface 261 for direct contact with a human eye's capsular diaphragm and a surrounding flange 262. The washer-like base member 430 includes a central throughgoing bore 431 through which the central convex surface 261 extends therethrough.

FIGS. 26 to 29 show the posterior capsule plates 208, 246 and 260 can be optionally additionally formed with a bulge control element 270 for centering anterior bulging. The bulge control elements 270 typically have a height between about 0.4 mm to about 0.6 mm relative to their leading surfaces. Such bulge control elements 270 preferably have the same refractive index as the rest of the optical members for avoiding aberrations at their interface. The bulge control elements 270 can have a spherical shape, a flattened bell shape, and the like.

While the invention has been described with respect to a limited number of embodiments, it will be appreciated that many variations, modifications, and other applications of the invention can be made within the scope of the appended claims.

The invention claimed is:

1. An accommodating intraocular lens (AIOL) capsule for implantation in a human eye having a visual axis, a sclera of tough connective tissue, an annular ciliary sulcus, and a sphincter-like ciliary body for tensioning a capsular diaphragm in an anterior direction along the visual axis on its relaxation from a contracted ciliary body state to a relaxed ciliary body state, the AIOL capsule for use with a rigid haptics system having a longitudinal axis and a haptics main body with at least two elongated generally C-shaped haptics extending therefrom in opposite directions in a plane perpendicular to the human eye's visual axis, each haptics terminating in an attachment plate having at least one pointed puncturing member for penetrating the tough connective tissue of the human eye's sclera for self-anchoring implantation in the human eye's annular ciliary sulcus at at least two spaced apart stationary anchor points for retaining the AIOL in the human eye, the haptics each including a Vertical Adjustment Mechanism adjacent the haptics main body deformable on localized heating by an external energy source for enabling post implantation in situ selective axial displacement of the AIOL along the human eye's visual axis relative to the at least two spaced apart stationary anchor points, the AIOL capsule having a longitudinal axis intended to be co-directional with the human eye's visual axis on implantation therein and comprising a capsule housing including a transparent anterior capsule plate, a transparent posterior capsule plate parallel and opposite said anterior capsule plate, and a capsule ring extending between said anterior and posterior capsule plates and having a leading rim connected to said anterior capsule plate and a trailing rim connected to said posterior capsule plate, said anterior capsule plate, said posterior capsule plate and said capsule ring bounding a hermetic cavity filled with a transparent capsule filling, said anterior capsule plate having an exposed leading surface and said posterior capsule plate having an exposed trailing surface, said trailing surface capable of undergoing repeated back and forth flexing relative to said capsule ring on application and in the absence of an axial compression force thereagainst from a posterior direction, said leading surface anteriorly bulging along the human eye's visual axis on application of said axial compression force and reverting to its non-flexed position in the absence of said compression force, whereby the AIOL capsule has a continuously variable Diopter strength ranging between a first Diopter strength in a non-compressed state and a second Diopter strength different than said first Diopter strength in a compressed state on application of said axial compression force.

2. The AIOL capsule according to claim 1 wherein said capsule housing includes a monolithic bowl-like capsule shell formed from said anterior capsule plate and said capsule ring for bounding said cavity, and said posterior capsule plate for rear side mounting on said bowl-like capsule shell for sealing said cavity.

3. The AIOL capsule according to claim 1 wherein said capsule housing includes a filleted leading internal surface for bounding a hermetic cavity with a rounded leading rim adjacent said anterior capsule plate.

4. The AIOL capsule according to claim 1 wherein said capsule housing includes an angled leading internal surface for bounding a hermetic cavity with a cone section shape converging in an anterior direction along the AIOL capsule's longitudinal axis.

5. The AIOL capsule according to claim 1 wherein said capsule 30 housing includes a converging tubular wall extending rearwards from a juncture between said anterior capsule plate and said capsule ring for bounding a hermetic cavity with a cone section shape converging in a posterior direction along the AIOL capsule's longitudinal axis.

6. The AIOL capsule according to claim 5 wherein said converging tubular wall has a trailing rim protruding beyond said capsule ring's trailing rim in a posterior direction along the AIOL capsule's longitudinal axis.

7. The AIOL capsule according to claim 1 wherein said posterior capsule plate includes a central capsule filling displacement member having a trailing surface and a peripheral annular flange having a trailing surface wherein said capsule filling displacement member's trailing surface protrudes posteriorly with respect to said annular flange's trailing surface along the AIOL capsule's longitudinal axis whereby said posterior capsule plate has a stepped trailing surface.

8. The AIOL capsule according to claim 7 wherein said capsule filling displacement member has a planar trailing surface.

9. The AIOL capsule according to claim 1 wherein said posterior capsule plate has a convex trailing surface.

10. The AIOL capsule according to claim 1 wherein said posterior capsule plate has a convex front surface for assisting said anterior 25 bulging.

* * * * *